United States Patent
Yanagita

(10) Patent No.: US 7,388,974 B2
(45) Date of Patent: Jun. 17, 2008

(54) MEDICAL IMAGE PROCESSING APPARATUS

(75) Inventor: Akiko Yanagita, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 702 days.

(21) Appl. No.: 10/947,461

(22) Filed: Sep. 21, 2004

(65) Prior Publication Data

US 2005/0070783 A1    Mar. 31, 2005

(30) Foreign Application Priority Data

Sep. 30, 2003    (JP)    ............................. 2003-341912

(51) Int. Cl.
   *G06K 9/00*    (2006.01)
(52) U.S. Cl. .................. 382/128; 382/224; 378/28
(58) Field of Classification Search ................ 382/100, 382/128, 129, 130, 131, 132, 133, 155, 168, 382/172, 181, 224, 232, 243, 260, 274, 276, 382/305; 600/425, 300; 715/738; 706/46; 398/109; 378/21, 28

See application file for complete search history.

(56) References Cited

U.S. PATENT DOCUMENTS

| | | | | |
|---|---|---|---|---|
| 4,739,521 A * | 4/1988 | Akimoto | ..................... | 398/109 |
| 5,235,510 A * | 8/1993 | Yamada et al. | ............. | 600/300 |
| 5,807,256 A * | 9/1998 | Taguchi et al. | ............. | 600/425 |
| 6,734,880 B2 * | 5/2004 | Chang et al. | ................ | 715/738 |
| 6,748,099 B1 * | 6/2004 | Kawata | ...................... | 382/132 |
| 7,245,754 B2 * | 7/2007 | Goto | .......................... | 382/128 |
| 7,280,992 B2 * | 10/2007 | Nitz | ............................ | 706/46 |

* cited by examiner

*Primary Examiner*—Seyed Azarian
(74) *Attorney, Agent, or Firm*—Squire, Sanders & Dempsey L.L.P.

(57) ABSTRACT

A medical image processing apparatus including: a diagnosis aid information generation section to generate diagnosis aid information by analyzing a medical image; a diagnosis aid information generation selection section to select whether to generate the diagnosis aid information, based on accessory information of the medical image; and an image output section to output the medical image and/or the generated diagnosis aid information to an image output apparatus.

8 Claims, 9 Drawing Sheets

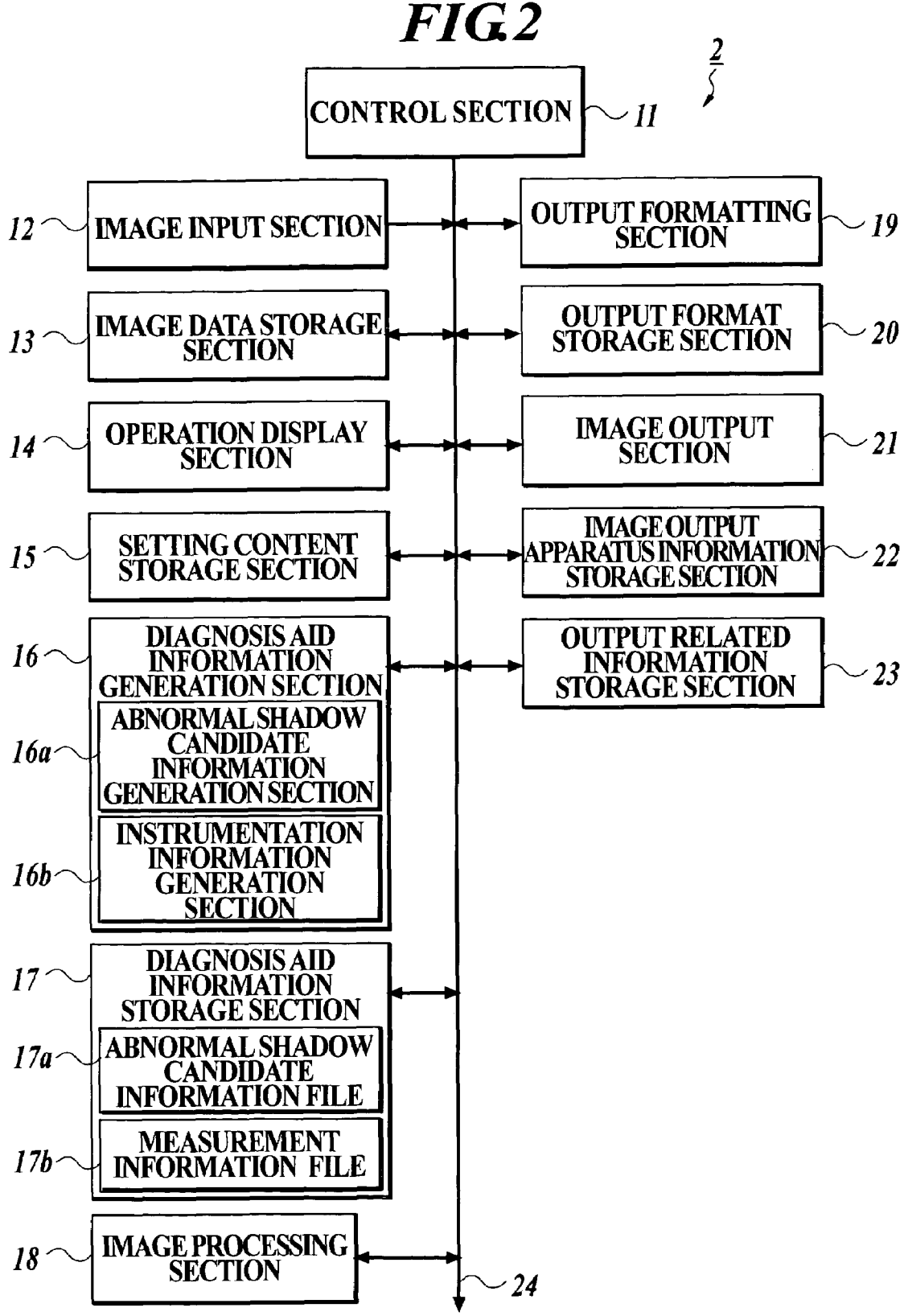

FIG.3

| ACCESSORY INFORMATION | | | | DIAGNOSIS AID INFORMATION GENERATION | DIAGNOSIS AID INFORMATION OUTPUT | OUTPUT CHANNEL | OUTPUT FORMAT | ... |
|---|---|---|---|---|---|---|---|---|
| RADIOGRAPHING REGION | RADIOGRAPHING POSTURE | EXAMINATION DEPARTMENT | EXAMINATION PURPOSE | | | | | |
| MAMMOGRAM | MLO | RADIOLOGY DEPARTMENT | MEDICAL EXAMINATION | ○ | ○ | 1 | A | ... |
| MAMMOGRAM | MLO | RADIOLOGY DEPARTMENT | DETAILED EXAMINATION | ○ | ○ | 1 | B | ... |
| MAMMOGRAM | MLO | SURGICAL DEPARTMENT | DETAILED EXAMINATION | ○ | ○ | 2 | C | ... |
| MAMMOGRAM | ENLARGED SPOT | SURGICAL DEPARTMENT | DETAILED EXAMINATION | ○ | × | – | – | ... |
| ABDOMEN | FRONT | RADIOLOGY DEPARTMENT | OUTPATIENT | × | × | – | – | ... |
| ... | | | | ... | ... | ... | ... | ... |

△MICROCALCIFICATION CLUSTERS

△MASS SHADOW

| RADIOGRAPH ID (171a) | DIAGNOSIS AID INFORMATION | | |
|---|---|---|---|
| | ABNORMAL TYPE (171b) | POSITION INFORMATION (171c) | SIZE (171d) |
| 20030101001 | MASS SHADOW | (100,1200) | 225mm² |
| 20030101002 | MICRO CALCIFICATION CLUSTER | (300,700) | 300mm² |
| 20030101003 | NODULAR SHADOW | (400,500) | 310mm² |
| ⋮ | ⋮ | ⋮ | ⋮ |

| RADIOGRAPH ID (172a) | DIAGNOSIS AID INFORMATION | | |
|---|---|---|---|
| | MEASUREMENT TARGET (172b) | POSITION INFORMATION (172c) | MEASUREMENT RESULT (172d) |
| 20030102001 | CHEST - CARDIOTHORACIC RATIO (%) | (200,1200),(700,1200), (1340,1200),(1800,1200) | 40 |
| 20030102002 | OSSA MEMBRI INFERIORIS - BONE LENGTH (cm) | (300,1200),(300,100) | 75 |
| 20030102003 | SCOLIOSIS - COBB ANGLE (DEGREE) | (900,500),(1000,770), (1000,1000) | 20 |
| ⋮ | ⋮ | ⋮ | ⋮ |

FIG. 7

| OUTPUT CHANNEL | IMAGE RECORDING APPARATUS / IMAGE DISPLAY APPARATUS | TRAY | OUTPUT SIZE | MAXIMUM RECORDING DENSITY | ... |
|---|---|---|---|---|---|
| 1 | 3a | T1 | SEXTO | 4.0 | ... |
| 2 | 3b | T3 | QUARTO | 3.0 | ... |
| 3 | 4 | — | — | — | ... |
| ... | ... | ... | ... | ... | ... |

… # MEDICAL IMAGE PROCESSING APPARATUS

BACKGROUND OF THE INVENTION

1. Field of the Invention

The present invention relates to a medical image processing apparatus which is capable of generating and outputting the corresponding diagnosis aid information by analyzing a medical image.

2. Description of Related Art

A conventional system for aiding a doctor to diagnose is already known, wherein the diagnosis aid information such as a detection result of the abnormal shadow candidates is added to the medical image which is used for screening, and outputted to a CRT monitor, an LED, or the like. For example, a technique is disclosed which switches the image output destination corresponding to the detection result of the abnormal shadow candidates (e.g. refer to JP-Tokukai-2000-342559).

The medical image and diagnosis aid information vary in output format and image output apparatus (e.g. a monitor, an image recording apparatus) with the individual diagnosis purpose as well as the image usage. However, the conventional approach suffers from being too complicated in that it requires a user, according to the individual diagnosis purpose as well as the image usage, to specify the output destination of the medical image and the diagnosis aid information, and the output format.

SUMMARY OF THE INVENTION

In view of the aforementioned problems, it is therefore an object of the present invention to provide a medical image processing apparatus which outputs the medical image and the diagnosis aid information automatically and appropriately corresponding to the individual diagnosis purpose as well as the image usage, enabling to easily and quickly refer and take full advantage of the diagnosis aid information. Hence, this helps the doctor to improve his diagnostic performance as well as working efficiency.

According to a first aspect of this invention, the medical image processing apparatus comprises: a diagnosis aid information generation section to generate diagnosis aid information by analyzing a medical image; a diagnosis aid information generation selection section to select whether to generate the diagnosis aid information based on accessory information of the medical image; and an image output section to output the medical image and/or the generated diagnosis aid information to an image output apparatus.

In accordance with the first aspect, whether to generate the diagnosis aid information is based on the accessory information of the medical image such as radiographing region, radiographing posture, examination department, and examination purpose or the like. Therefore, the diagnosis aid information can be generated automatically, when necessary, corresponding to examination purpose and image application.

Preferably, the medical image processing apparatus further comprises an image output selection section to select whether to output the medical image and/or the diagnosis aid information to the image output apparatus based on the accessory information of the medical image.

In accordance with this invention, whether to output the medical image and/or the diagnosis aid information to the image output apparatus is based on the accessory information of the medical image such as radiographing region, radiographing posture, examination department, and examination purpose or the like. Therefore, the medical image and the diagnosis aid information can be outputted automatically, when necessary, corresponding to examination purpose and image application.

Preferably, the medical image output section comprises a plurality of output channels which correspond to a plurality of image output apparatuses, and the processing apparatus further comprises an output channel selection section to select one channel from the plurality of output channels, to which the medical image and/or the diagnosis aid information is outputted based on the accessory information of the medical image.

In accordance with the invention, the selection of one channel from the plurality of output channels, to which the medical image and/or the diagnosis aid information is outputted, is based on the accessory information of the medical image such as radiographing region, radiographing posture, examination department, and examination purpose or the like. Therefore, the medical image and the diagnosis aid information can be outputted from an appropriate output channel corresponding to examination purpose and image application.

Preferably, the medical image processing apparatus further comprises an information distributing destination selection section to select an image output apparatus from the plurality of image output apparatuses as an information distributing destination of the medical image and/or the diagnosis aid information, and the image output section outputs the medical image and/or the diagnosis aid information to the selected image output apparatus.

In accordance with the invention, the selection of an information distributing destination of the medical image and/or the diagnosis aid information is based on the accessory information of the medical image such as radiographing region, radiographing posture, examination department, and examination purpose or the like. Therefore, the medical image and the diagnosis aid information can be outputted from an appropriate image output apparatus corresponding to examination purpose and image application.

Preferably, the medical image processing apparatus further comprises an output format selection section to select an output format for the medical image and/or the diagnosis aid information according to the accessory information of the medical image; and an output formatting section to manipulate the medical image and/or the diagnosis aid information according to the selected output format.

In accordance with the invention, an output format for the medical image and/or the diagnosis aid information is chosen based on the accessory information of the medical image such as radiographing region, radiographing posture, examination department, and examination purpose or the like, and the medical image and/or the diagnosis aid information is manipulated according to the chosen output format. Therefore, the medical image and the diagnosis aid information can be outputted in an output format corresponding to examination purpose and image application.

Preferably, the output format selection section selects the output format from a plurality of output format candidates which are stored in advance.

In accordance with the invention, the output format can be chosen from a plurality of output format candidates that are stored in advance.

Preferably, the medical image processing apparatus further comprises an output related information storage section to store information of a selection result of the diagnosis aid information generation selection section and diagnosis aid information corresponding to the medical image when the diagnosis aid information has been generated so as to correspond the information of the selection result and the diagnosis aid information to the medical image.

In accordance with the invention, when re-outputting a once inputted image, it is not necessary to conduct again whether to generate the diagnosis aid information and the calculation of the diagnosis aid information. Therefore the processing time can be shortened.

Preferably, the output related information storage section stores information of a selection result of the image output selection section so as to correspond the information of the selection result of the image output selection section to the medical image.

In accordance with this invention, when re-outputting a once inputted image, it is not necessary to conduct again whether to output the diagnosis aid information and the calculation of the diagnosis aid information. Therefore the processing time can be shortened.

Preferably, the output related information storage section stores information of a selection result of the output format selection section so as to further correspond the information of the selection result of the output format selection section to the medical image.

In accordance with the invention, when re-outputting a once inputted image, it is not necessary to choose again an output format. Therefore the processing time can be shortened.

Preferably, the output related information storage section stores information of a selection result of the output channel selection section so as to correspond the information of the selection result of the output channel selection section to the medical image.

In accordance with the invention, when re-outputting a once inputted image, it is not necessary to choose again an output channel. Therefore the processing time can be shortened.

Preferably, the output related information storage section stores information of a selection result of the information distributing destination selection section so as to further correspond the information of the selection result of the information distributing destination selection section to the medical image.

In accordance with the invention, when re-outputting a once inputted image, it is not necessary to choose again an image output apparatus as the information distributing destination. Therefore the processing time can be shortened.

Preferably, the medical image processing apparatus further comprises an output related information modification section to modify contents which are stored in the output related information storage section.

In accordance with the invention, the content of the stored output related information can be modified, therefore, when re-outputting a once inputted image, it is possible to generate the output image where various conditions are modified as needed.

Preferably, the medical image processing apparatus further comprises: a setting section to set a relation between information of whether to generate the diagnosis aid information and accessory information of the medical image; and a setting content storage section to store a content which is set by the setting section, and the diagnosis aid information generation selection section reads out the setting content which is stored in the setting content storage section, and carries out a selection according to the accessory information of the medical image.

In accordance with the invention, the relation between the information on whether to generate the diagnosis aid information, and the accessory information of the medical image is set in advance and stored. Therefore it is possible to easily choose whether to generate the diagnosis aid information according to the accessory information of the medical image.

Preferably, the medical image processing apparatus further comprises a setting section to set a relation between information of whether to generate the diagnosis aid information and accessory information of the medical image; and a setting content storage section to store a content which is set by the setting section, and the diagnosis aid information generation selection section reads out the setting content which is stored in the setting content storage section, and carries out a selection according to the accessory information of the medical image.

In accordance with the invention, the relation between the information on whether to output the medical image and/or the diagnosis aid information, and the accessory information of the medical image is set in advance and stored. Therefore it is possible to easily choose whether to output the medical image and/or the diagnosis aid information according to the accessory information of the medical image.

Preferably, the medical image processing apparatus further comprises a setting section to set a relation between information of the output channel and accessory information of the medical image; and a setting content storage section to store a content which is set by the setting section, and the output channel selection section reads out the setting content which is stored in the setting content storage section, and carries out a selection according to the accessory information of the medical image.

In accordance with the invention, the relation between the information of the output channel and the accessory information of the medical image is set in advance and stored. Therefore it is possible to easily choose an output channel according to the accessory information of the medical image.

Preferably, the medical image processing apparatus further comprises a setting section to set a relation between information of an output apparatus of the information distributing destination and accessory information of the medical image; and a setting content storage section to store a content which is set by the setting section, and the information distributing destination selection section reads out the setting content which is stored in the setting content storage section, and carries out a selection according to the accessory information of the medical image.

In accordance with the invention, the relation between the information of the image output apparatus of the information distributing destination and the accessory information of the medical image is set in advance and stored. Therefore it is possible to easily choose an image output apparatus as the information distributing destination according to the accessory information of the medical image.

Preferably, the medical image processing apparatus further comprises a setting section to set a relation between information of an output format and accessory information of the medical image; and a setting content storage section to store a content which is set by the setting section, and the output format selection section reads out the setting content which is stored in the setting content storage section, and carries out a selection according to the accessory information of the medical image.

In accordance with the invention, the relation between the information of the output format and the accessory information of the medical image is set in advance and stored.

Therefore it is possible to easily choose an output format according to the accessory information of the medical image.

Preferably, the medical image processing apparatus further comprises a setting content modification section to modify the contents which are stored in the setting content storage section.

In accordance with the invention, the setting content which is stored in the setting content storage section can be modified.

Preferable, the medical image processing apparatus further comprises an image output apparatus information storage section to store information of the image output apparatus corresponding to each of the plurality of output channels; and an output formatting section to determine an output format according to image output apparatus information which is stored in the image output apparatus information storage section and to manipulate the medical image and/or the diagnosis aid information according to the output format which has been determined.

In accordance with the invention, the medical image and/or the diagnosis aid information can be manipulated in an output format which is suitable for the image output apparatus of the output destination.

Preferably, the medical image processing apparatus further comprises an image output apparatus information storage section to store information of the plurality of image output apparatus; and an output formatting section to determine an output format according to image output apparatus information which is stored in the image output apparatus information storage section and to manipulate the medical image and/or the diagnosis aid information according to the output format which has been determined.

In accordance with the invention, the medical image and/or the diagnosis aid information can be manipulated in an output format which is suitable for the image output apparatus of the information distributing destination.

Preferably, the medical image processing apparatus further comprises a diagnosis aid information storage section to store diagnosis aid information generated by the diagnosis aid information generation section; and an output instruction section to instruct an output of the diagnosis aid information, and the output formatting section to read out the diagnosis aid information from the diagnosis aid information storage section according to an instruction from the output instruction section and to manipulate the diagnosis aid information according to an output format, and the image output section outputs the manipulated diagnosis aid information to the image output apparatus.

In accordance with the invention, the generated diagnosis aid information is ready to be outputted at any time.

Preferably, the medical image processing apparatus further comprises a formatted output diagnosis aid information storage section to store diagnosis aid information manipulated by the output formatting section; and an output instruction section to instruct an output of the diagnosis aid information, and the image output section to read out the manipulated diagnosis aid information from the formatted output diagnosis aid information storage section according to an instruction from the output instruction section and to output the manipulated diagnosis aid information to the image output apparatus.

In accordance with the invention, the manipulated diagnosis information is stored in advance, and on receiving an instruction to output the diagnosis aid information, the manipulated diagnosis aid information is read out and outputted to the image output apparatus. Therefore, it is possible to easily re-output the diagnosis aid information.

Preferably, the diagnosis aid information generation section detects an abnormal shadow candidate in the medical image and generates diagnosis aid information which contains position information within the medical image relating to the detected abnormal shadow candidate.

In accordance with the invention, it is possible to reduce the omission of a lesion by a doctor and alleviate the screening load of a doctor.

Preferably, the diagnosis aid information generation section conducts measurement on an image within the medical image, and generates diagnosis aid information which contains position information within the medical image relating to the detected abnormal shadow candidate.

In accordance with the invention, it is possible to improve the accuracy of the image measurement by a doctor, and alleviate the screening load of a doctor.

BRIEF DESCRIPTION OF THE DRAWINGS

The invention will become more fully understood from the detailed description given hereinbelow and the accompanying drawings which are given by way of illustrating only, and thus are not intended as a definition of the limits of the invention, and wherein;

FIG. 2 is a block diagram illustrating the mechanical configuration of the image processing apparatus 2 of FIG. 1;

FIG. 3 illustrates one example of the setting table which is stored in a setting content storage section 15 of FIG. 2;

FIG. 5A illustrates one exemplary data storage of the abnormal shadow candidate file 171 which the diagnosis aid information storage section 17 stores;

FIG. 5B illustrates one exemplary data storage of the measurement information file 172 which the diagnosis aid information storage section 17 stores;

FIG. 7 illustrates the data storage of the image output apparatus information storage section 22 of FIG. 2;

DETAILED DESCRIPTION OF THE PREFERRED EMBODIMENTS

The embodiments of the invention are detailed as follows with reference to the drawings.

Figure 1:
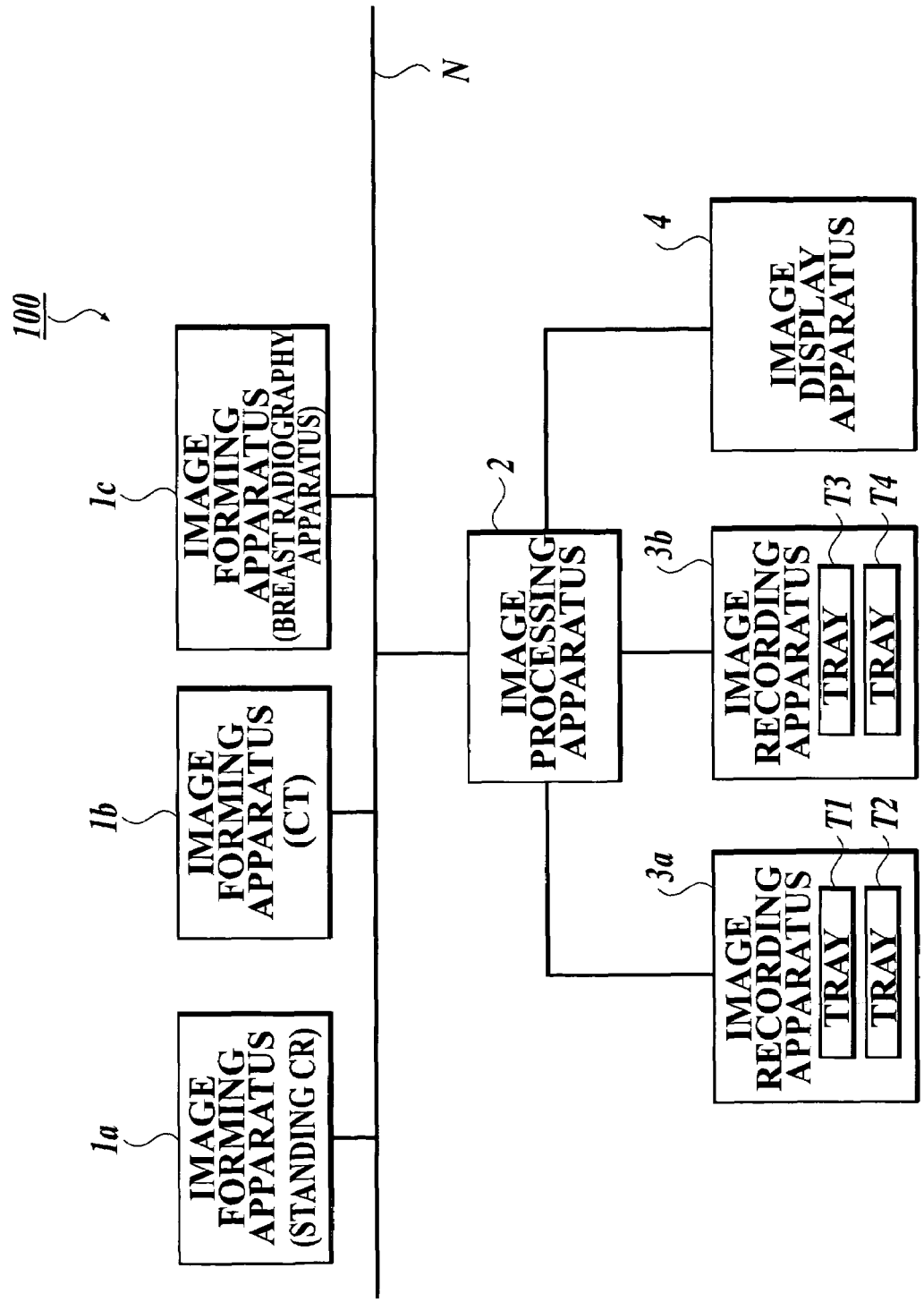
FIG. 1 illustrates the entire configuration of a medical image processing system 100 in accordance with the invention.

FIG. 1 is a conceptual diagram illustrating the entire configuration of the medical image processing system 100 in accordance with the embodiment. As illustrated in FIG. 1, the medical image processing system 100 is so connected that data can be transmitted and received between the image forming apparatus 1a-1c, and the image processing apparatus 2 through a network N. The image recording apparatus 3a, 3b, and the image display apparatus 4 are connected respectively to the image processing apparatus 2. The image processing apparatus 2 is so configured that data can be transmitted and received between the image recording apparatus 3a, 3b and the image display apparatus 4.

The network N can be various kinds of networks, being a LAN (Local Area Network), or a WAN (Wide Area Network), or an internet or the like. While wireless communication or infrared communication, when permitted by a medical institution such as a hospital, can be introduced as well, it is desirable to encrypt the information to be transmitted and received which contains important patient information. The DICOM (Digital Image and Communication in Medicine) standard is commonly used as the communication system in hospitals, and DICOM MWM (Modality Worklist Management) or DICOM MPPS (Modality Performed Procedure Step) is used for communicating between each component of the network N.

The image forming apparatus 1a-1c comprise a CR (Computed Radiography), an FPD (Flat Panel Detector), a CT (Computed Tomography), an MRI (Magnetic Resonance Imaging), a mammography, an ultrasonic detection apparatus, or the like, whereby a subject is radiographed and a medical images is formed after the radiographed image is digitized. In the embodiment, the image forming apparatus 1a is a standing CR, the image forming apparatus 1b is a CT and the image forming apparatus 1c is a breast radiography apparatus.

The image forming apparatus 1a-1c meet the DICOM standard, and the image accessory information of the DICOM can be inputted or generated automatically. The image forming apparatus 1a-1c output the formed medical image data together with the corresponding image accessory information to the image processing apparatus 2 through the network N, but when the image forming apparatus 1a-1c don't meet the DICOM standard, a DICOM converting apparatus, which is not shown in the figure, can be used instead for inputting the accessory information.

For the medical image accessory information, for example, one can name the following: (1) patient information such as patient name, patient ID, age, sex of the patient; (2) examination information such as radiographing data, radiograph ID, radiographing region, radiographing condition (e.g. body posture, radiographing direction), radiographing apparatus, examination department, examination purpose, doctor in charge; (3) image data information such as number of pixels, number of bits, predetermined output size, reading-out pixel size, maximum recording density.

The image processing apparatus 2 is a medical image processing apparatus which, according to the accessory information of the medical image data to be inputted from the image forming apparatus 1a-1c, chooses various conditions to be employed to the medical image, and then conducts various processing on the medical image according to the chosen conditions. Fox example, based on the accessory information of the medical image, the image processing apparatus 2 chooses: presence or absence of the generation of the diagnosis aid information for the medical image, presence or absence of the medical image output, presence or absence of the diagnosis aid information output, format for outputting the medical image and the diagnosis aid information, and output channels, and among others.

The image data inputted from the image processing apparatus 2 is reproduced as a visual image, and the image recording apparatus 3a, 3b output the reproduced hardcopy. The image recording apparatus 3a and 3b vary each other in recording property.

The recording apparatus 3a is, for example, a photothermal silver halide type recording apparatus, whereby a latent image is recorded on a transmission recording media (a film) by laser exposure based on the image data inputted from the image processing apparatus 2, followed by heat developing processing to visualize the latent image. The image recording apparatus 3a has two trays, T1 and T2. The size of films stored in T1 is sexto while the size of films stored in T2 is quarto. The maximum recording density (Dmax) of the film loaded in the trays T1 and T2 is 4. 0, i.e. Dmax=4. 0.

The image recording apparatus 3b is an image recording apparatus which records image data inputted from the image processing apparatus 2 on a transmission type recording media (e.g. a film) by a photothermal silver halide type recording apparatus system or a thermal system. The image recording apparatus 3b has two trays, T3 and T4. The size of films stored in T3 is quarto while the size of films stored in T4 is folio. The maximum recording density (Dmax) of the films loaded into Trays T1 and T2 is 3.0, i.e. Dmax=3.0.

The image display apparatus 4 can be a CRT (Cathode Ray Tube), or a liquid crystal display, or a plasma display, and the like, whereon the image data inputted from the image processing apparatus 2 is displayed.

The internal configuration of the image processing apparatus 2 is explained as follows.

Major components of the image processing apparatus 2 are illustrated in FIG. 2. In FIG. 2, the image processing apparatus 2 comprises a control section 11, an image input section 12, an image data storage section 13, an operation display section 14, a setting content storage section 15, a diagnosis aid information generation section 16, a diagnosis aid information storage section 17, an image processing section 18, an output formatting section 19, an output format storage section 20, an image output section 21, an image output position information storage section 22, an output related information storage section 23 and the like. Each component is connected to each other through a bus 24.

The control section 11 comprises a CPU (Central Processing Unit), a ROM (Read Only Memory), a RAM (Random Access Memory) and the like. The CPU reads out system programs and processing programs which are stored in the ROM, frees them to the RAM, controls each component of the image processing apparatus 2 according to the freed programs, and carries out various kinds of processing, including an image output control processing which is to be explained later.

The image input section 12 obtains the image data of the medical image (hereinafter referred to image data D1) from the image forming apparatus 1a-1c through the network N. In addition, the image input section 12 can also be configured as to read out the image data D1 from various recording media wherein the image data D1 is stored, e.g. a CD-ROM, a floppy (registered trademark) and the like. Moreover, such a configuration can also be introduced in the image input section 12 so that it has an interface for connecting to image forming apparatus such as a CR, a CT, a mammography, an FPD, an MRI, and an ultrasonic detection apparatus through cables, and obtain the medical image data D1 by these apparatus.

The image data D1 varies in effective pixel size with radiographing region as well as examination purpose when being obtained from the above configurations. For example, for mammography, it is preferable to have an effective pixel size of less than 200 µm. Furthermore, less than 100 µm is much more appreciated. Therefore, in order to take full advantage of the image processing apparatus 2, it is desirable to use an inputted image data D1 having an effective pixel size of, for example, less than 50 μm.

In addition, on inputting the image data D1, the image input section 12 also inputs the accessory information relating to the image data D1, and output the image data D1 with the accessory information being corresponded to the image data D1 when outputting the image data D1 to the image data storage section 13.

The image data storage section 13 employs, when necessary, data compression technique to the image data D1 which is inputted from the image input section 12, and then stores the image data D1. A data compression algorithm, either lossless one or lossy one, which employs such techniques as JPEG, DPCM (Differential Pulse Code Modulation), or wavelet, can be adopted. However, the lossless one is preferred because it doesn't deteriorate the diagnostic information during compression stage.

For a small scale examination wherein the amount of data inputted from the image input section 12 is not that large, enabling the image data D1 to be stored in a magnetic disk without being compressed. In this case, the image data D1 is fast to store and read in comparison with a magneto optical disk. Because a short cycle time is required for reading an image, essential image data D1 is stored in the semiconductor memory.

The operation display section 14 comprises a LCD (Liquid Crystal Display) which displays status of various kinds of buttons and apparatus on the display, and previews the medical image and the diagnosis aid information which are to be outputted to the image recording apparatus 3a, 3b and the image display apparatus 4. The LCD is covered with a pressure sensitive type (a resistive membrane pressure type) touch panel where transparent electrodes are arranged therein with a lattice pattern. The XY coordinates of the emphasis pushed downed with a finger are detected in terms of voltage, and the detected position signal is then outputted as an operation signal. In addition, the display apparatus and the input apparatus can be two separate ones. A CRT, an LCD, a plasma display, or the like, can be used as a display apparatus. A keyboard equipped with function keys corresponding to various functions such as a cursor key, a numeric input key, an enter key, and a pointing device such as a mouse can be use as an input apparatus.

The operation display apparatus 14 is an output instruction section whereby the output instruction of the diagnosis aid information is inputted by a user. For example, on inputting the output instruction of the identification information and the diagnosis aid information by a user, the output instruction of the diagnosis aid information corresponding to the inputted identification information is outputted to the control section 11. Besides, the operation display section 14 is used to input various setting contents and modification contents as a setting section, a setting content modification section and an output related information modification section, which are all to be explained.

The setting content storage section 15 comprises a HDD (Hard Disc), a semiconductor nonvolatile memory and the like. As shown in FIG. 3, data showing the accessory information of the image data D1 (e.g. data showing radiographing region (mammography, abdomen, etc.), data showing radiographing posture (MLO (Medio-Lateral Oblique), enlarged spot, front, etc.), data showing examination department (radiology department, surgical department, etc.), data showing examination purpose (medical examination, detailed examination, outpatient, etc.)), and data showing various conditions of processing corresponding to the image data (e.g. data showing presence or absence of the diagnosis aid information generation (○ showing presence, x showing absence), data showing presence or absence of the medical image output (○ showing presence, x showing absence), data showing presence or absence of the diagnosis aid information output (○ showing presence, x showing absence), data identifying the output channel (1,2, etc.), data identifying the output format (A, B, C, etc.)) are corresponded to each other and stored as a setting table by the setting content storage section 15. The setting table stores the content of the relation between the accessory information of the image data D1, which is set and inputted from the operation display which is a setting section, and various conditions such as presence or absence of the diagnosis aid information generation, presence or absence of the medical image output, present or absence of the diagnosis aid information output, output format, output channel.

The setting content stored in the setting content storage section 15 can always be modified by a user through an input from the operation display section 14, which is a setting content modification section.

The diagnosis aid information generation section 16 comprises an abnormal shadow candidate information generation section 16a and a measurement information generation section 16b.

Figure 4A:
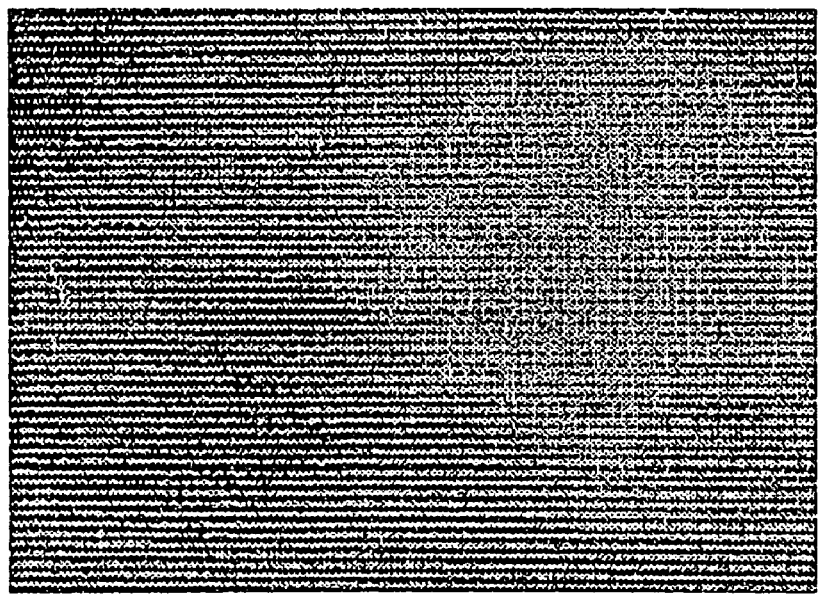
FIG. 4A illustrates one exemplary microcalcification cluster.
Figure 4B:
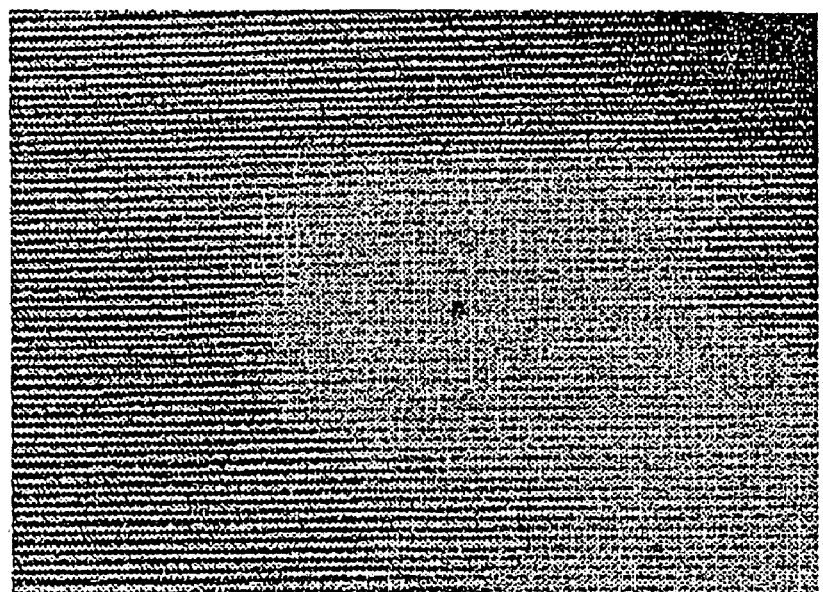
FIG. 4B illustrates one exemplary mass shadow.

The abnormal shadow candidate information generation section 16a, on receiving an instruction from the control section 11 to generate the diagnosis aid information for the image data D1, reads out the image data D1 from the image data storage section 13, carries out image analysis to detect a candidate which is thought to be an abnormal shadow such as a microcalcification cluster in the mammography, a mass shadow, a nodular shadow in the chest image, and generates the diagnosis aid information which contains information on a position within the image of the abnormal shadow candidate. FIG. 4A illustrates one exemplary microcalcification cluster. The presence of clustered microcalcification indicates a high possibility of the presence of early cancer, enabling it to be an important indicator for detecting early cancer. In mammography, the microcalcification is seen as an approximately cone-shaped whitish circular shadow. The mass shadow illustrated in FIG. 4B is a mass with a somewhat large size, and is seen as, in the mammography, a whitish circular shadow having an approximately gaussian distribution.

For detecting mass shadow, methods from the following publications can be adopted.

(1) Mass Shadow

A method by comparing left and right mammas (Med. Phys., Vol.21. No.3, pp.445-452)

A method by using Iris filter (IEICE transactions (D-II), Vol.J75-D-II, no.3, pp.663-670, 1992)

A method by using Quoit filter (IEICE transactions (D-II), Vol.J76-D-II, no.3, pp.279-287, 1993)

A method by binarization based on histogram of pixel values of divided mamma areas (JAMIT Collected Papers of Frontier Lecture, pp.84-85, 1995)

A method using a minimum direction differential filter for taking the minimum output from a large number of Laplacian filters having polarity (IEICE transactions (D-II), Vol.J76-D-II, no.2, pp.241-249, 1993)

A method classifying a mass shadow as benignity or malignity by using fractal dimension (Medical Imaging technology 17(5), pp.577-584, 1999)

For detecting abnormal shadow candidates of the microcalcification cluster, methods from the following publications can be adopted.

(2) Microcalcification Clusters a method of eliminating a false positive candidate based on an optical density difference of shadow figure, or standard deviation of a boundary density difference of the localized area where suspected calcification in a mamma area is present (IEEE Trans. Biomed. Eng. BME-26(4):213-219, 1979)

a detection method by using an image on which Laplacian filter processing is applied (IEICE Trans. (D-II), Vol.J71-D-II, no.10, pp.1994-2001, 1988)

a detection method using a morphologically analyzed image in order to inhibit a background pattern such as mammary gland or the like (IEICE Trans. (D-II), Vol.J71-D-II, no.7, pp.1170-1176, 1992).

For detecting other abnormal shadow candidates, methods from the following publications can be adopted.

(3) Detection of Nodules Shadow from Chest Images JP-Tokukaihei-06-121792

(4) Detection of Interstitial Diseases Shadow from Chest Images

JP-Tokukaihei-02-185240.

On receiving an instruction from the control section 11 to generate the diagnosis aid information for the image data, the measurement information generation section 16b reads out the image data D1 from the image data storage section 13, performs image measurement, and generates the diagnosis aid information which contains information on a position within the image relating to the measurement result. Among the image measurements are, for example, the measurement of the cardiothoracic ratio which is used to diagnoses the cardiomegalia from the chest image; the measurement of the bone length of the assa membri inferioris from the lower limb image, which is used for planning an operation; the measurement of the Cobb angle which is used for diagnosing the scoliosis form the spine image. The measurement can be either configured so as to be processed automatically (e.g. Medical Physics, Vol.17, No.3, pp.342-350; JP-Tokukaihei-07-381) or configured so as to be calculated according to the information inputted by using such pointing device as a touch pen and a mouse with an operator watching the image which is being displayed on the displaying menu of the operation section 14 (e.g. JP-Tokukaihei-08-256993).

The diagnosis aid information storage section 17 comprises: a file 171 by which the diagnosis aid information generated by the abnormal shadow candidate information generation section 16a is stored so as to be corresponded to the image data D1; and a file 172 by which the diagnosis aid information generated by the measurement information generation section 16b is stored so as to be corresponded to the image data D1.

The abnormal shadow candidate 171 comprises, as shown in FIG. 5A, a radiograph ID region 171a, an abnormal type region 171b, a position information region 171c, a size region 171d and the like. The abnormal type, the position information and the size, which are the diagnosis aid information generated by the abnormal shadow candidate information generation section 17a for the image data D1 specified by the radiograph ID, are stored so as to be corresponded to each other, and the image data D1 stored in the image data storage section 13 and the diagnosis aid information in the abnormal shadow candidate file 171 are corresponded to each other.

The abnormal type region 171b stores as abnormal type the data that shows the type of the detected abnormal shadow candidates (e.g. a mass shadow, a microcalcification cluster, a nodular shadow, etc.). The position information region 171c stores as position information the data that shows the coordinates of the center of gravity of the abnormal shadow candidates (e.g. (x, y)=(100, 1200), (300, 700), (400, 500)). The position information is not limited to the aforementioned, for example, the coordinate that shows the image region of the abnormal shadow candidates may be used instead. In addition, the distance to a distinctive normal issue may be used, for example, in the case where the radiographing region is chest, the position showing the distance between the center of gravity of the abnormal shadow candidate and the center of gravity of the lung region which is a distinctive normal tissue may be used. A distinctive normal tissue refers to a biological tissue whose position rarely changes, e.g. internal organs such as heart, lung, and spine; and bone, and requires preferably a tissue that can be an indicator of variation with time for the position of the abnormal shadow candidates. The size information region 171d stores as the size the data that shows the area occupied by the image region of the abnormal shadow candidates (e.g. 225 mm2, 300 mm2, 310 mm2). The size information may be represented by the average distance or the maximum distance from the center of gravity to the border of the abnormal shadow candidates.

The measurement information file 172 comprises, as shown in FIG. 5, a radiograph ID region 172a, a measurement target region 172b, a position information region 172c, a measurement result region 172d and the like. The measurement target, the position information and the measurement result, which are the diagnosis aid information generated by the measurement information generation section 17a for the image data D1 specified by the radiograph ID, are stored so as to be corresponded to each other, and the image data D1 stored in the image data storage section 13 and the diagnosis aid information in the abnormal shadow candidate file 172 are corresponded to each other.

The measurement target region 172b stores as the measurement target the data that shows measurement target (e.g. chest-cardiothoracic ratio, ossa membri inferioris-bone length, scoliosis-Cobb angle). The position information region 172c stores as the position information the data that shows the coordinate of the image of the place which is used in the measurement (e.g. {(200, 1200), (700, 1200), (1340, 1200), (1800, 1200)}, {(300, 1200), (300, 100), (900, 500), (1000, 770), (1000, 1000)}). The measurement result region 172d stores as the measurement result the data that shows measurement result (e.g. 40, 75, 20). The unit of the measurement result is set in advance for each individual measurement target.

In addition, each storing mode of the diagnosis aid information is not limited to the aforementioned ones. For example, the diagnosis aid information can be stored in the head information of the image data D1 in the image data storage section 13.

On receiving an instruction from the control section 11 to output the medical image of the image data D1 and/or the diagnosis aid information, the image processing section 18 then reads out the image data D1 from the image data storage section 13 and employs image processing on the image data D1 according to the output format instructed from the control section 11 before outputting to the output formatting section 19. The image processing techniques employed here includes gradation processing which adjusts image contrast, frequency processing which adjusts image sharpness, dynamic range compression processing which suppresses an image with a high dynamic range in a legible density scope without decreasing the detailed contrast of an object, and so on.

When receiving an instruction from the control section 11 to output the medical image, the image processing section 18 employs image processing on the image data D1 and generates a diagnosis medical image that is suitable for diagnosing. The degradation processing is employed to the image data under certain processing conditions that are determined so that a contrast is sufficient for screening a lesion shadow. Two examples are given hereinbelow to show how to determine the degradation processing conditions.

Method 1

Figure 6A:
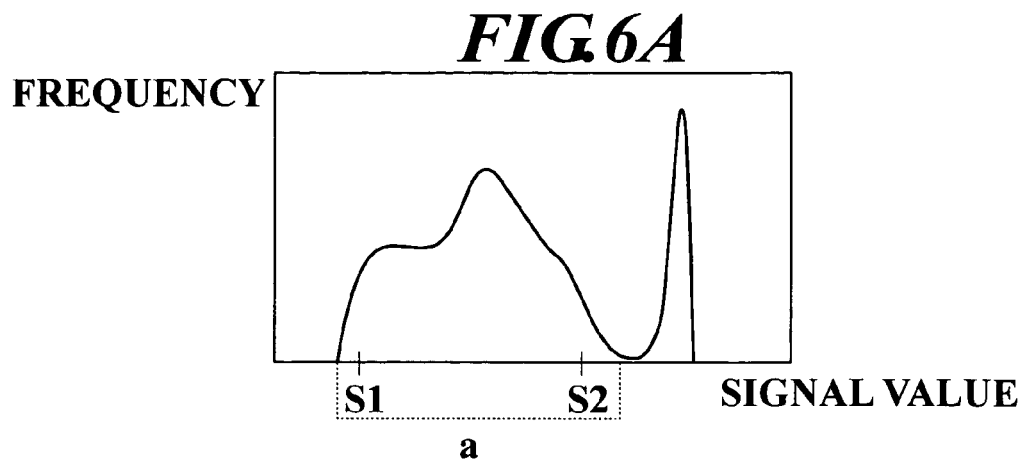
FIG. 6A illustrates one exemplary histogram analysis.

First, the image data D1 is analyzed, and an image area that corresponds to an desirable portion of the object is determined by using a method as disclosed in JP-Tokukaihei-03-218578 which extracts the pulmonary area from the chest image or using another method which extracts a deep breast area from the mammography as published in the Journal of the Japan Association of Breast Cancer Screening (Vol.17, No.1, pp.87-102, 1998). Secondly, as shown in FIG. 6A, analyze the area histogram using the methods of JP-Tokukaisho-63-262141 or JP-Tokukaihei-08-62751, and then determine an area a that corresponds to a diagnostically important signal area. After determining the area a, calculate the cumulative histogram in the area a. Obtain the signal values S1 and S2 that correspond to the predetermined cumulative histogram (e.g. 5%, 95%) and determine these S1 and S2 as base signal values.

Figure 6B:
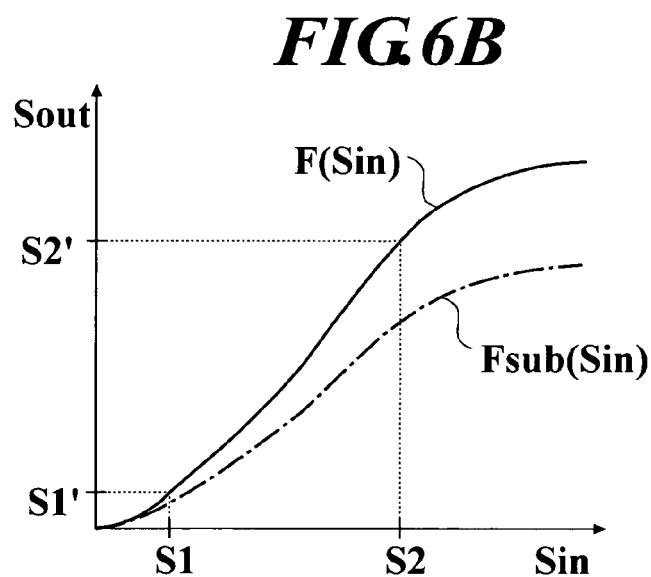
FIG. 6B illustrates one exemplary method for determining a degradation transform curve.

Next, as disclosed in JP-Tokukaisho-59-83149, transform the base degradation curve, which is chosen from different kinds of base degradation curves, to obtain a degradation transform curve corresponding to the function F (Sin) which transforms respectively the predetermined base signal values S1, S2 in the axis of the signal value of Sin as shown in FIG. 6B, with respect to the axis of the output signal value Sout, to S1', S2' respectively.

$$Sout=F(Sin) \quad (1)$$

where S1' and S2' are values corresponding respectively to the base output density D1 and D2 which are predetermined. The relation between the output signal value Sout and the density D is determined by the properties of the image output apparatus (i.e. the image recording apparatus 3a, 3b, or the image display apparatus 4) which is the output destination whereto an image is outputted. The properties of the image output apparatus which is the output destination, such as image output apparatus information (machine type, output image size (film size: horizontal and vertical pixel number), maximum and minimum recording density, density resolution, degradation property, frequency property) are stored in the image output apparatus information storage section 22 which is to be explained later. The relation between the output signal value Sout and the density D is obtained, with reference to the image output apparatus storage section 22, by the image processing section 18 based on the property of the apparatus which corresponds to the output channel that has been instructed from the control section 11.

Method 2

Figure 6C:
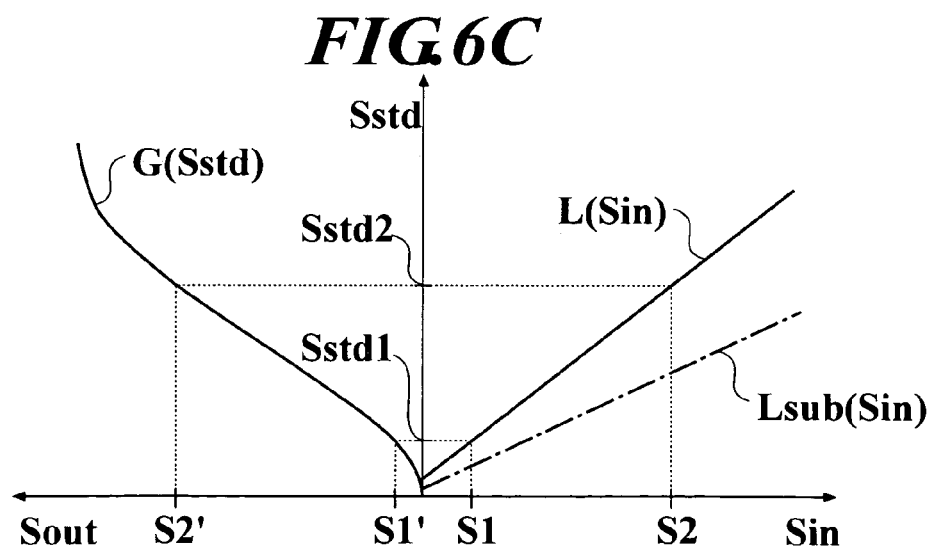
FIG. 6C illustrates a method for determining a standardized line.

First, the base signal values S1 and S2 are obtained using the same method as method 1. Next, as shown in FIG. 6C, a standard degradation curve G(Sstd) which is chosen from the standard degradation curves is prepared in advance. Then determine the standardized line represented by a linear function L(Sin) which transforms the base signal values S1, S2, with respect to the input signal value Sin, to the predetermined standardized signal values Sstd1, Sstd2 respectively.

$$Sstd=L(Sin) \quad (2)$$

where the standardized signal values Sstd1, Sstd2 are determined as signal values which output the output signal values S1, S2 corresponding to the standard density D1, D2 which are determined respectively when the standard degradation curve Gstd is used for transforming.

The relation between input and output in the degradation processing, when expressed using a curve graph where the horizontal axis is the logarithm of X-ray which has passed through an object while the vertical axis is output density, the average slope of the curve between the output densities of two predetermined points (e.g. 0.25 and 2.0) is referred as the average gradient.

As the gradient processing conditions of the diagnosis medical image, in order to observe the lesion shadow in detail, a high average gradient is required. Specifically, for mammography, a value of more than 2.0, for radiographing area other than mammography, a value of more than 1.5 are preferred respectively. In addition, for mammography, a value of more than 2.5, for radiographing area other than mammography, a value of more than 2.0 are much more preferred respectively.

Prior to the gradation processing, a radiation field recognition processing is carried out to detect the radiation field, and various image processing conditions are set based on the image data within the recognized radiation field, making it possible to perform appropriately the image processing on the image which is though to be necessary for diagnosing, therefore such an embodiment is preferable. Techniques for detecting the radiation field, for example, those methods disclosed in JP-Tokukaisho-63-259538, JP-Tokukaihei-05-7579, JP-Tokukaihei-07-181609 can be applied.

As for frequency processing, for example, by using non-sharpness mask processing technique as disclosed in JP-Tokukosho-62-62373, JP-Tokukosho-62-62376, and multiple resolution technique as disclosed in JP-Tokukaihei-09-44645, image sharpness is controlled.

By dynamic range compression processing, the low spatial frequency components of the image is controlled, causing the entire wide image of the dynamic range to be suppressed in a density range which is easy-to-recognize. Methods for dynamic range compression processing, for example, a technique as disclosed in JP-266318 can be adopted.

Here, the image processing conditions for frequency processing and dynamic range compression processing are determined by, along with the analysis results of the image data D1, the property of the image output apparatus which is the output destination for outputting. The image processing section 18, when receiving an instruction from the control section 11 to output the diagnosis aid information, performs image processing on the image data D1 corresponding to the output format of the diagnosis aid information which is instructed from the control section 11. For example, as the diagnosis aid information output format, when format A is instructed from the control section 11, which adds to the diagnosis aid image, other than the diagnosis medical image, an annotation which shows diagnosis aid information, the gradation processing, frequency processing, dynamic range compression processing are carried out under image processing conditions which are different from those when the diagnosis medical image is created, and the diagnosis aid image which is suitable for the reference of the diagnosis aid information is created. Also, when format B is instructed from the control section 11, which adds the diagnosis aid information to a schema image, a schema image is created. Hereinbelow explained is image processing corresponding to the cases where formats A, B are instructed respectively.

Format A

During the degradation processing, the image processing section 18 suppresses the entire image within a density range that is easy to recognize, determines the degradation processing conditions for representing the position relation of the annotation in a way that is easy to understand, and carries out the degradation processing on the image data D1 under the determined degradation processing conditions.

When using the above method 1 to determine the degradation processing conditions for generating the diagnosis medical image, after the degradation transform curve F(Sin) of the diagnosis medical image is determined, the degradation transform curve of the diagnosis aid image is then determined based on the determination. A way to determine the degradation transform curve of the diagnosis aid image is by multiplying a predetermined coefficient a ($\alpha$<1.0) to F(Sin) so as to create the degradation transform curve F sub(sin) of the diagnosis aid image (refer to FIG. 6B).

When using the above method 2 to determine the degradation processing conditions for generating the diagnosis medical image, after the standardized line L (Sin) of the diagnosis medical image is determined, by multiplying a predetermined coefficient $\alpha$ ($\alpha$<1.0) to L (Sin), the standardized line L sub(sin) of the diagnosis aid image is then created (refer to FIG. 6C).

Alternatively, as the base output density Dsub1 and Dsub2 of the diagnosis aid image, values smaller than base output density D1 and D2 of the diagnosis medical image are set in advance, the degradation processing condition of the diagnosis medical image can be determined by using Dsub1 and Dsub2 and following the above method 1 or method 2 of the degradation processing condition of the diagnosis medical image. Here, the values of Dsub1 and Dsub2 are set so that the value of (Dsub2−Dsub1) is smaller than the value of (D2−D1).

In order to represent the diagnosis aid image from the entire object to the background in an easy to recognize density range, a degradation processing condition with a relatively low average gradient is set. Specifically, for mammography, a value smaller than 3.5, for the raidographing region other than mammography, a value smaller than 3.0 are preferred respectively. Furthermore, for mammography, a value smaller than 3.0, for the raidographing region other than mammography, a value smaller than 2.5 are preferred respectively. In addition, preferably, the average gradient of the diagnosis aid image is a value lower than 80% of the diagnosis medical image.

The degradation transform curves F(Sin), Fsub(Sin) or the standardized lines L(Sin), Lsub(Sin) are determined in such a manner so that the average gradient of the diagnosis aid image is relatively smaller than the average gradient of the diagnosis medical image, allowing a sufficient contrast for screening a lesion shadow in the diagnosis medical image whose purpose is medical examination, and allowing the entire image to be suppressed in an easy to recognize density range in the diagnosis aid image whose purpose is as a reference, which enables the annotation position relation to be represented in an easy to understand manner.

Moreover, the degradation processing condition can be determined in the following manner.

Reverse the degradation transform curve F(Sin) of the diagnosis medical image or the standardized line L(Sin) along the vertical axis.

Reverse along the vertical axis the degradation transform curve Fsub(Sin) which has been obtained so that the average gradient is smaller than the diagnosis medical image or the standardized line L(Sin).

The standardized line or the degradation transform curve is determined in such a way that the average gradient of the diagnosis aid image has a value whose sign is opposite to, the average gradient of the degradation transform curve of the diagnosis medical image or the standardized line; or is opposite to the average gradient of the degradation transform curve which has been obtained in such a way that the average gradient is smaller than the diagnosis medical image or the standardized line, allowing a sufficient contrast for screening a lesion shadow in the diagnosis medical image whose purpose is medical examination, and allowing the boundary between the object and the background to be represented in an easy to recognize density range by reversing the black and while of the image, which enables both the object and the annotation position relation to be represented in an easy to understand manner. This kind of processing is especially effective to mammography image.

For frequency processing, the sharpness of the image is controlled by non-sharpness mask processing as disclosed in JP-Tokukosho-62-62373, JP-Tokukosho-62-62376, multi-resolution method as disclosed in JP-Tokukaihei-09-44645. In this case, the frequency processing condition is determined in such a way so that the low frequency component is relatively attenuated compared with the low frequency component of the diagnosis medical image, allowing a sufficient contrast for screening a lesion shadow in the diagnosis medical image whose purpose is medical examination, and allowing the entire image to be suppressed in an easy to recognize density range in the diagnosis aid image whose purpose is as a reference, which enables the annotation position relation to be represented in an easy to understand manner.

As an alternative manner for relatively attenuating the low frequency component of the diagnosis aid image, in the dynamic range compression processing, the dynamic range compression processing condition may be determined so that the low frequency component of the diagnosis aid image, compared with diagnosis medical image, is compressed to a larger extent.

Format B

The image processing section 18 extracts contour by analyzing the image data D1 which is read out from the image data storage section 13, and generates a schema. For contour extracting methods, as disclosed in JP-Tokukaisho-63-240832, when focusing on one line or row of the image data D1, a specified pattern (a local minimum point, a point having a local maximum gradient, or a point having a local minimum gradient) where the relation of back and forth data value in a one-dimensional density data array is determined in advance, is regarded as a contour point of that line or row, and the contour points of lines or rows within a necessary range are obtained. Connecting these points lead to a contour line. Other known contour extracting methods may also be adopted (e.g. for mammography, Medical Electronics and Biomedical Engineering, Vol.39, No.4, pp.297-304, 2001).

The output formatting section 19 reads out from the output format storage section 20 an output format which is instructed from the control section 11, conducts image size adjustment, rotation, reversion, cropping and synthesizing on the diagnosis medical image and the diagnosis aid image which are obtained by performing image processing on the image data D1 in the image processing section 18 based on the output format, and outputs the manipulated image to the image output section 21.

For the diagnosis aid image, the output formatting section 19 reads out, based on the output format instructed from the control section 11, from the abnormal candidate shadow file 171 or the measurement information file 172 the diagnosis aid information corresponding to image data D1, and generates a corresponding annotation (the diagnosis aid information represented with a symbol, a character, a marker). When necessary, an annotation is added to the diagnosis aid image according to the output format (e.g. the above formats A, B). Moreover, with reference to the accessory information of the image data 1, information like patient ID, patient name, radiographing date is added to the diagnosis medical image and the diagnosis aid image.

In the cases where the diagnosis aid image is outputted to the image display apparatus 4 like a CRT, an LCD, the annotation may be, in accordance with the image data, outputted as overlay information which meets the DICOM standards. In this case, by an operation from the image display apparatus 4, the annotation may overlay on the image or disappear from the image.

The diagnosis aid image may be an image which represents the entire object area, or part of the image based on the diagnosis aid information.

For purposes of being able to easily recognize the position and size of a structure in the diagnosis aid image, either a scale may be added to the diagnosis aid image or an evenly spaced grid may be overlaid thereon.

Other than annotation, information which can be represented by characters like abnormal shadow candidates or measurement information may be added to an area which is outside the image area of the diagnosis aid image.

For example, in the case where the radiographing region is mamma, the output formatting section 19 synthesizes the medical images of left and right mammas, which are taken in the same direction, to one image data by making the two images facing each other. Here, the position registration processing based on the image data analysis can be adopted (JP-Tokukai-2000-287957).

When the output format specified from the control section 11 is, for example, like formats A and B in which cases the diagnosis medical image and the diagnosis aid image are outputted respectively, the output formatting section 19 adds to the predetermined area of each image the same identification information showing that they are generated from the same original image (image data D1) for the purpose of relating to each other. The accessory information can be a patient ID or identification information for special use. Furthermore, in the case where the diagnosis medical image and the diagnosis aid information are outputted respectively, information showing if one image has been outputted is added to the other image.

The output format storage section 20 stores multiple-types of output formats.

The image output section 21 has multiple channels corresponding to multiple image output apparatus (the image recording apparatus and its trays, the image display apparatus), and outputs the diagnosis medical image data or the diagnosis aid image data to the image output apparatus which is the output destination corresponding to an output channel chosen by the control section 11. The information of the image output apparatus (the image recording apparatus or its trays) corresponding to each channel is stored in the image output apparatus information storage section 22.

The image output apparatus information storage section 22 is connected to the image processing section 2. Possible information of each image recording apparatus (or its trays) and of the image display apparatus, which is outputted from the image processing apparatus 2, is stored so as to be corresponded to the output channel. FIG. 7 shows one example of the image output apparatus position information storage section 22. As shown in FIG. 7, the image recording apparatus, types of the image display apparatus, output target image, output image size (film size: vertical and horizontal pixel number), maximum and minimum recording density, density resolution, degradation property, frequency property and so on are so stored in the image output apparatus information storage section 22 as to be corresponded to the output channel.

The output related information relating to the image outputted from the image output section 21 is stored, by the output related information storage section 23, so as to be corresponded to the image data D1 which is the original image and which is stored in the image data storage section 13. The image data D1 and the output related information are, for example, corresponded to each other through the radiograph ID or the like. The output related information includes various conditions which are determined for outputting image and outputted diagnosis aid information, for example, generated diagnosis aid information, presence or absence of the diagnosis aid information generation, presence or absence of the diagnosis aid information output, presence or absence of the diagnosis medical image output, output format, output channel, the accessory information of the medical image (image data D1), or the like. By these kinds of information, when a once outputted image is outputted again, there is no need to perform a second time such tasks as diagnosis aid information calculation, output format determination, determination of the presence or absence of the diagnosis aid information generation and of the output, enabling the processing time to be reduced.

The content stored in the output related information storage section 23 is made modifiable by an input from the operation section 14, which an output related information modification section, enabling to generate a modified output image corresponding to various conditions when re-outputting a once outputted image.

This configuration of the image processing apparatus is explained in the above. The diagnosis aid information generation section 16, the image processing section 18 and the output formatting section 19 can be operated according to software processing which is based on the cooperation between a CPU and programs stored in a ROM, or can be operated by a special hardware. Furthermore, the image data storage section 13, the diagnosis aid information storage section 17, the output format storage section 20, the image output apparatus information storage section 22, and the output related information storage section 23 can be made to store in the same recording apparatus, the same recording medium.

Next, the operation will be explained.

Figure 8:
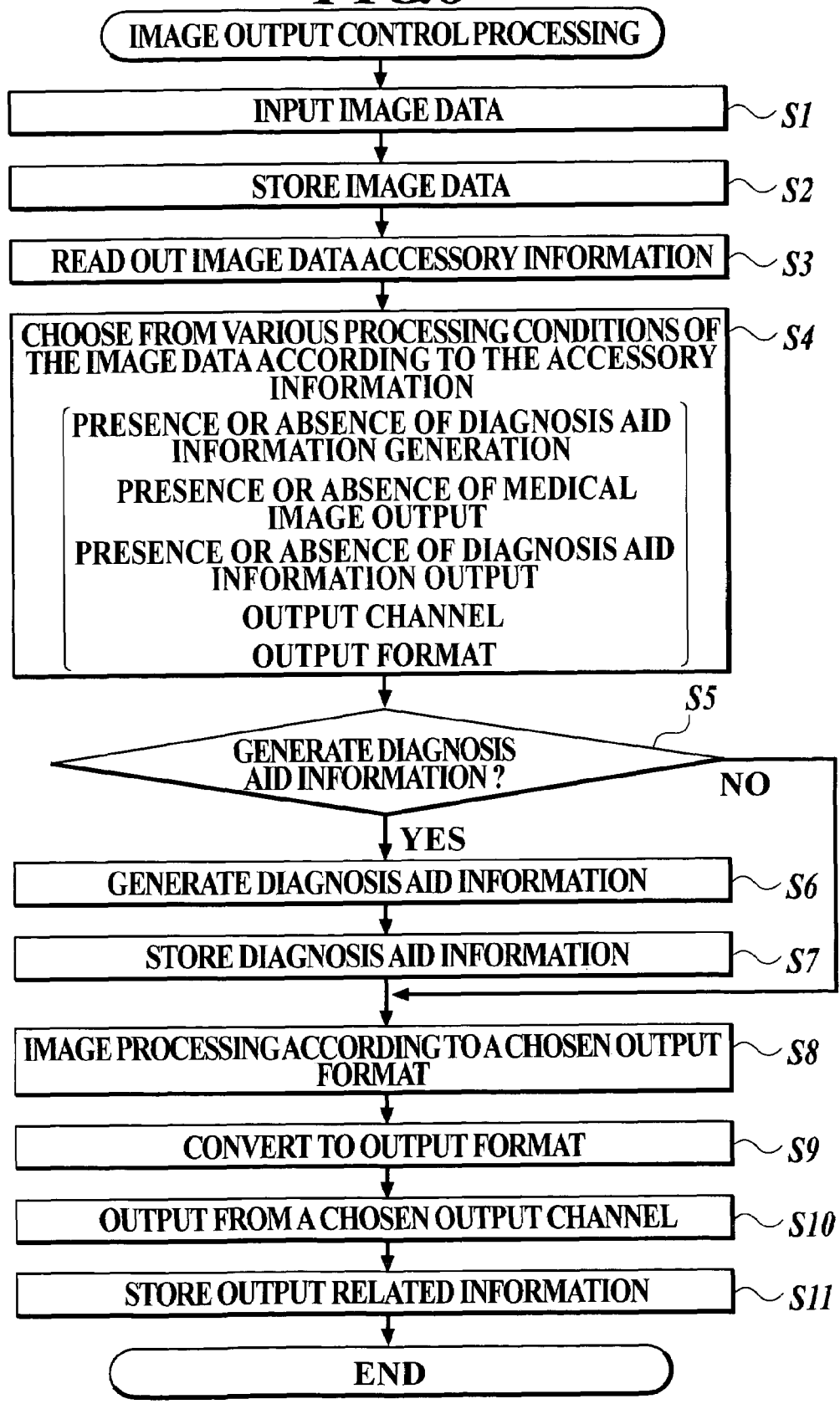
FIG. 8 is a flow chart illustrating the image output control processing which is carried out by the control section 11 of FIG. 2.

Referring to FIG. 8, the image output control processing conducted by the control section 11 is explained.

First, on inputting the image data D1 and its accessory information from the image input section 12 (step S1), the image data D1 is stored in the image data storage section 13 (step S2), and at the same time, the accessory information of the image data D1 is read out (step S3). The setting table stored in the setting content storage section 15 is referred, and various conditions of the processing on the image data D1 are chosen and determined based on the accessory information (step S4). In other words, in the present step, based on the accessory information of the image data D1, the following selection tasks are conducted: choose if generate the diagnosis aid information (presence or absence of the generation), if output the medical image and the diagnosis aid information (presence or absence of the output), the selection of an output channel in the case where the diagnosis information is outputted, the selection of output format. The selection results are outputted to each section. By conducting the step S4, the diagnosis aid information generation selection section, the image output selection section, the output channel selection section, output formatting selection, which are all described in the claims, are implemented.

Under the chosen conditions in step S4, when the diagnosis aid information generation is chosen not to execute (step S5: NO), the processing goes to step S8, when the diagnosis aid information generation is chosen to execute (step S5: YES), the diagnosis aid information of the image data D1 is generated by the diagnosis aid information generation section 16 (step S6), and is stored in a predetermined file of the diagnosis aid information storage section 17 (step S7).

In step S8, based on the conditions determined in step S4, e.g. the presence or absence of the medical image and of the diagnosis aid information and the chosen output format, image processing is performed on the image data D1, by the image processing section 18 (step S8). Then the output format chosen in step S3 is read out from the output format storage section 20 by the output formatting section 19, and manipulation is conducted on the diagnosis medical image, the diagnosis aid medical image and the diagnosis aid information, which are generated in the image processing section 18 (step S9). Then in the image output section 21, the data of the medical image and/or the diagnosis aid information is outputted from the output channel chosen in step S3 (step S10), the output related information is stored in the output related information storage section 23 (step S11). On inputting an instruction from the operation display section 14 to output the once outputted diagnosis aid information, the diagnosis aid information, the output format and the output channel are read out from the output related information storage section 23 by the control section 11, manipulated by the output formatting section 19, and outputted by the image output section 21. In addition, methods for re-outputting the once outputted diagnosis aid information are not limited to the above described. For example, the re-outputting method can be configured in such a way that the information stored in the diagnosis aid information storage section 17 is read out and manipulated to the output format by the output formatting section 19 and outputted from the image output section 21; or be configured in such a way that a formatted output diagnosis aid information storage section is provided which stores the formatted output diagnosis aid information from where the formatted output diagnosis aid information is read out by the image output section 21 and outputted from the image output section 21.

As explained above, in accordance with the image processing apparatus 2, based on the accessory information of the image data, and by referring to the setting content storage section 15, various selections are conducted such as the selection of the presence or absence of the diagnosis aid information generation, the selection of the presence or absence of output of the medical image and the diagnosis aid information, the selection of the output channel in the case where the output of the medical image and the diagnosis aid information is present, the selection of the output format, based on these chosen conditions, image processing and manipulation are performed on the image data, the diagnosis medical image and/or the diagnosis aid information are outputted.

Therefore, the accessory information which contains information such as examination department, rodiographing region, rodiographing posture and examination purpose makes it possible to automatically output a suitable image corresponding to the examination purpose, the image application, and the like. As a result, a doctor is able to consult and take good advantage of the diagnosis information easily and quickly, which enables the doctor's diagnosis performance and working efficiency to be improved.

For example, the image observation condition such as brightness and size of the schaukasten which is to be used, the property of the monitor varies from examination department to examination department. However, with the invention, the output format corresponding to each observation condition can be outputted automatically from the output apparatus.

Also, the output format and the presence or absence of the diagnosis aid information generation vary according to the examination purpose. However, the invention enables the processing to be automatically operated corresponding to each examination purpose. For example, for the purpose of medical examination, a simple output format is used; for the purpose of detailed examination, an output format showing detailed information is used. Furthermore, because a medical examination requires checking if a lesion is present, the diagnosis aid information is generated, but in a detailed examination, the lesion region is already known, hence, the diagnosis aid information is not generated.

Further, each doctor in charge has his own favorite output format. But in the invention if the output format is pre-set for each doctor in charge in the accessory information, the output format for each doctor in charge can be outputted automatically.

The necessity and output method vary according to each radiographing region and radiographing posture. But the invention enables an automatic processing corresponding to each radiographing region and radiographing posture. For example, the diagnosis aid information is configured to generate for mammogram, but is configured not to generate for a region other than mammogram. Also, the diagnosis aid information can be configured so as to be generated for an MLO or CC of the mammogram, and can be configured not to be generated for an enlarged spot of the mammogram.

In addition, the afore described embodiment shows only one ideal example of the medical image processing system 100, however, the invention is not limited to this.

For example, in the above embodiment, it is not limited to the case where various conditions, which correspond to the combination of radiographing region, radiographing posture, examination department, examination purpose, are set in a setting table. For example, the output channel, which corresponds to a combination of a predetermined output size, a reading pixel size and a maximum recording density, is set in the setting table, enabling to automatically output to an appropriate output destination corresponding to an image.

Also, for example, in the case where an output channel corresponding to the accessory information has been set in the setting table, but the output format is not set, the image output apparatus information of the output destination (e.g. the image recording apparatus, the image display apparatus) corresponding to a chosen channel based on the accessory information is read out from the image output apparatus information storage 23 by the output formatting section 19, an output format suitable for the output destination is determined and manipulated.

Also the selection of an output channel in the image forming apparatus 1a-1c can be manipulated in such a manner that the image recording apparatus which should output the diagnosis image or the diagnosis aid information is determined in advance, the name of the determined image recording apparatus is sent to the image processing apparatus 2 as accessory information, and in the image processing apparatus 2, an output channel corresponding to the name of the determined image processing apparatus based on the accessory information is selected.

Figure 9:
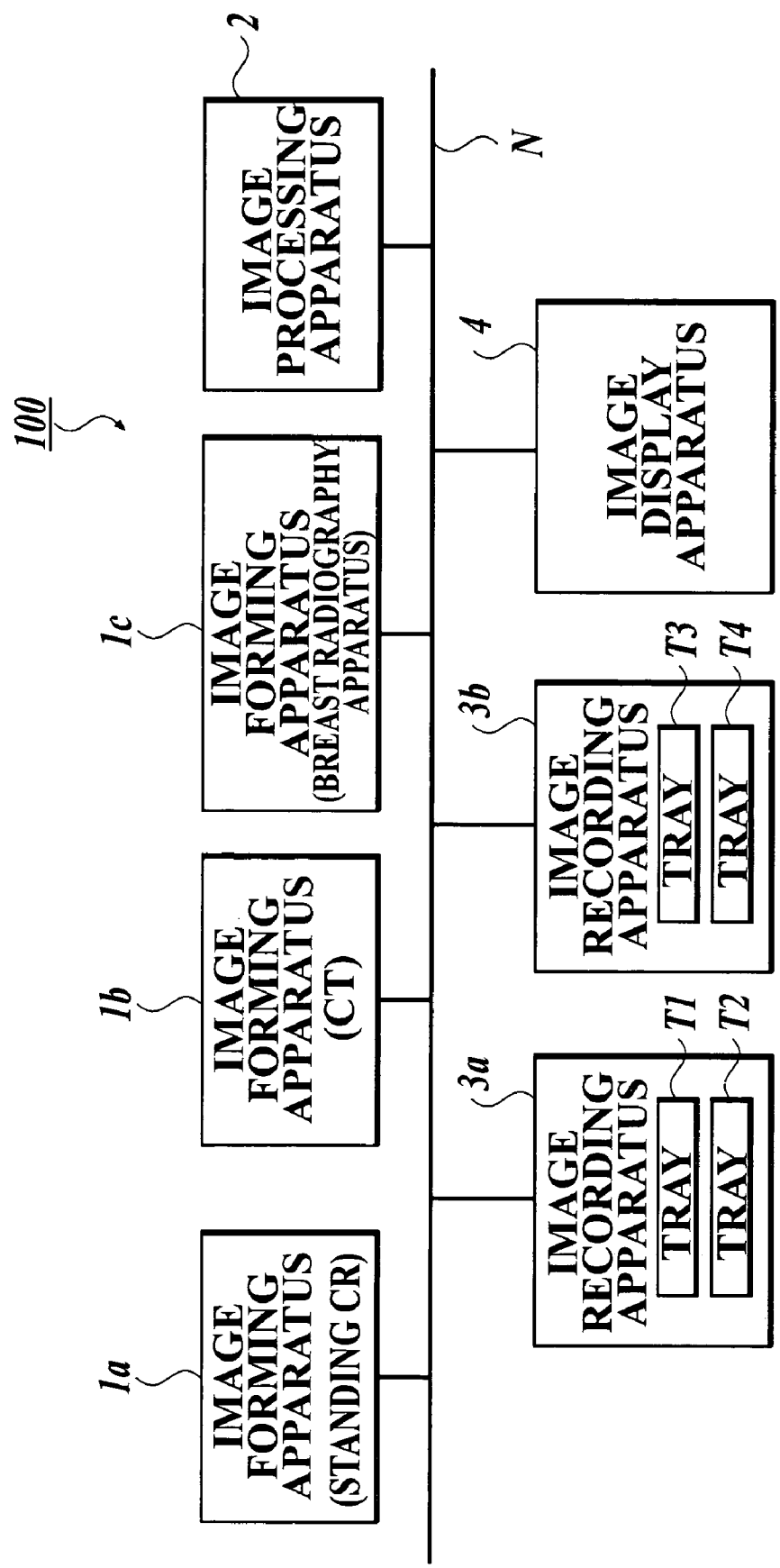
FIG. 9 illustrates a system configuration for the case where the image recording apparatus 3a, 3b and the image display apparatus 4 are connected to a network N.

Also, as shown in FIG. 9, a configuration can be manipulated in such a way that image output apparatus, i.e. the image recording apparatus 3a, 3b and the image display apparatus 4 are connected to the network N, and data transmission between the image processing apparatus 2 and these image output apparatus is carried out through the network N. In this case, the operation display section 14 which is a setting section, set and input the relation between the accessory information of the image data D1 and various conditions such as presence or absence of the diagnosis aid information generation, presence or absence of the medical image output, present or absence of the diagnosis aid information output, output format, and at the same time is capable of setting the relation between the image data D1 and the image output apparatus (e.g. the image output apparatus 3a, 3b (or their trays), the image display apparatus 4) which is the information distributing destination of the medical image and/or the diagnosis aid information. The data which shows the accessory information of the image data D1 and the data which shows various conditions corresponding to the image data D1 which includes data showing the image output apparatus which is the information distributing destination, are so stored, by the setting content storage section 15, as to be corresponded to each other. The image output section 21 is capable of outputting the medical image data or the diagnosis aid information data to the image output apparatus which is the information distributing destination of the medical image data or the diagnosis aid information data. In step S4 of the image output control processing to be carried out by the control section 11, the setting content storage section 15 is referred, the image output apparatus (information distributing destination selection section), which is the information distributing destination of the medical image and/or the diagnosis aid information, is chosen according to the accessory information. In step S10, the medical image data or the diagnosis aid information data is outputted to the image output apparatus chosen by the image output section 21. In step S11, the output related information, which includes the selection result of the image output apparatus of the information distributing destination, is stored in the output related information storage section 23.

And in the case where the configuration is as shown in FIG. 9, the operation can be in such a way that the image output apparatus information (information of image recording apparatus 3a, 3b (and their trays), and image display apparatus 4), which could be outputted from the image processing apparatus 2, is stored in the image output apparatus information storage section 22, when the image output apparatus corresponding to the accessory information has been set in the setting table of the setting content storage section 15 but the output format has not been set, the image output apparatus information relating to the image output apparatus which is the information distributing destination chosen according to the accessory information is read out from the image output apparatus information storage section 22 by the output formatting section 19, the output format which is suitable for the output destination is determined according to the image output apparatus information, and the medical image and/or the diagnosis aid information is manipulated.

Although the invention has been explained according to the embodiments, it should also be understood that the invention is not limited to the embodiments and that various changes and modifications may be made to the invention from the gist thereof. For example, the detailed configuration and detailed operation of each component of the medical image processing system 100 can be modified as needed.

The entire disclosure of Japanese Patent Application No. 2003-341912 filed on Sep. 30, 2003 including specification, claims, drawings and summary is incorporated herein by reference in its entirety.

What is claimed is:

1. A medical image processing apparatus, comprising:
   a diagnosis aid information generation section to generate diagnosis aid information by analyzing a medical image;
   a diagnosis aid information generation selection section to select whether to generate the diagnosis aid information, based on accessory information of the medical image; and
   an image output section to output the medical image and/or the generated diagnosis aid information to an image output apparatus, wherein the image output section comprises a plurality of output channels which correspond to a plurality of image output apparatuses;
   an output channel selection section to select one channel from the plurality of output channels, to which the medical image and/or the diagnosis aid information is outputted, based on the accessory information of the medical image;
   a setting section to set a relation between information of the output channel and accessory information of the medical image; and
   a setting content storage section to store a content which is set by the setting section,
   wherein the output channel selection section reads out the setting content which is stored in the setting content storage section, and carries out a selection according to the accessory information of the medical image.

2. The processing apparatus of claim 1, further comprising a setting content modification section to modify the contents which are stored in the setting content storage section.

3. A medical image processing apparatus, comprising:
   a diagnosis aid information generation section to generate diagnosis aid information by analyzing a medical image;

a diagnosis aid information generation selection section to select whether to generate the diagnosis aid information, based on accessory information of the medical image;

an image output section to output the medical image and/or the generated diagnosis aid information to an image output apparatus;

an information distributing destination selection section to select an image output apparatus from the plurality of image output apparatuses as an information distributing destination of the medical image and/or the diagnosis aid information, wherein the image output section outputs the medical image and/or the diagnosis aid information to the selected image output apparatus;

a setting section to set a relation between information of an output apparatus of the information distributing destination and accessory information of the medical image; and a setting content storage section to store a content which is set by the setting section, wherein the information distributing destination selection section reads out the setting content which is stored in the setting content storage section, and carries out a selection according to the accessory information of the medical image.

4. A medical image processing apparatus, comprising:

a diagnosis aid information generation section to generate diagnosis aid information by analyzing a medical image;

a diagnosis aid information generation selection section to select whether to generate the diagnosis aid information, based on accessory information of the medical image;

an image output section to output the medical image and/or the generated diagnosis aid information to an image output apparatus;

an output format selection section to select an output format for the medical image and/or the diagnosis aid information according to the accessory information of the medical image;

an output formatting section to manipulate the medical image and/or the diagnosis aid information according to the selected output format;

a setting section to set a relation between information of an output format and accessory information of the medical image; and a setting content storage section to store a content which is set by the setting section, wherein the output format selection section reads out the setting content which is stored in the setting content storage section, and carries out a selection according to the accessory information of the medical image.

5. A medical image processing apparatus, comprising:

a diagnosis aid information generation section to generate diagnosis aid information by analyzing a medical image;

a diagnosis aid information generation selection section to select whether to generate the diagnosis aid information, based on accessory information of the medical image;

an image output section to output the medical image and/or the generated diagnosis aid information to an image output apparatus, wherein the image output section comprises a plurality of output channels which correspond to a plurality of image output apparatuses;

an output channel selection section to select one channel from the plurality of output channels, to which the medical image and/or the diagnosis aid information is outputted, based on the accessory information of the medical image;

an image output apparatus information storage section to store information of the image output apparatus corresponding to each of the plurality of output channels; and an output formatting section to determine an output format according to image output apparatus information which is stored in the image output apparatus information storage section and to manipulate the medical image and/or the diagnosis aid information according to the output format which has been determined.

6. A medical image processing apparatus, comprising:

a diagnosis aid information generation section to generate diagnosis aid information by analyzing a medical image;

a diagnosis aid information generation selection section to select whether to generate the diagnosis aid information, based on accessory information of the medical image;

an image output section to output the medical image and/or the generated diagnosis aid information to an image output apparatus;

an information distributing destination selection section to select an image output apparatus from the plurality of image output apparatuses as an information distributing destination of the medical image and/or the diagnosis aid information, wherein the image output section outputs the medical image and/or the diagnosis aid information to the selected image output apparatus;

an image output apparatus information storage section to store information of the plurality of image output apparatus; and an output formatting section to determine an output format according to image output apparatus information which is stored in the image output apparatus information storage section and to manipulate the medical image and/or the diagnosis aid information according to the output format which has been determined.

7. A medical image processing apparatus, comprising:

a diagnosis aid information generation section to generate diagnosis aid information by analyzing a medical image;

a diagnosis aid information generation selection section to select whether to generate the diagnosis aid information, based on accessory information of the medical image;

an image output section to output the medical image and/or the generated diagnosis aid information to an image output apparatus;

an output format selection section to select an output format for the medical image and/or the diagnosis aid information according to the accessory information of the medical image;

an output formatting section to manipulate the medical image and/or the diagnosis aid information according to the selected output format;

a diagnosis aid information storage section to store diagnosis aid information generated by the diagnosis aid information generation section; and an output instruction section to instruct an output of the diagnosis aid information, wherein the output formatting section reads out the diagnosis aid information from the diagnosis aid information storage section according to an instruction from the output instruction section and manipulates the diagnosis aid information according to an output format, and the image output section outputs the manipulated diagnosis aid information to the image output apparatus.

8. A medical image processing apparatus, comprising:

a diagnosis aid information generation section to generate diagnosis aid information by analyzing a medical image;

a diagnosis aid information generation selection section to select whether to generate the diagnosis aid information, based on accessory information of the medical image;

an image output section to output the medical image and/or the generated diagnosis aid information to an image output apparatus;

an output format selection section to select an output format for the medical image and/or the diagnosis aid information according to the accessory information of the medical image;

an output formatting section to manipulate the medical image and/or the diagnosis aid information according to the selected output format;

a formatted output diagnosis aid information storage section to store diagnosis aid information manipulated by the output formatting section; and an output instruction section to instruct an output of the diagnosis aid information, wherein the image output section reads out the manipulated diagnosis aid information from the formatted output diagnosis aid information storage section according to an instruction from the output instruction section and outputs the manipulated diagnosis aid information to the image output apparatus.

* * * * *